United States Patent [19]

Dohara et al.

[11] Patent Number: 5,137,713

[45] Date of Patent: Aug. 11, 1992

[54] INSECTICIDAL AEROSOL

[75] Inventors: Kazunobu Dohara; Satoshi Sembo, both of Toyonaka, Japan

[73] Assignee: Sumitomo Chemical Company, Limited, Osaka, Japan

[21] Appl. No.: 411,889

[22] Filed: Sep. 25, 1989

[30] Foreign Application Priority Data

Nov. 11, 1988 [JP] Japan .................................. 63-286368

[51] Int. Cl.⁵ ................................................ A61L 9/04
[52] U.S. Cl. .......................................... 424/45; 424/70; 514/136; 514/392; 514/479; 514/521; 514/531
[58] Field of Search ................... 424/356, 273, 45, 70; 252/364; 428/447; 525/478; 514/75, 136, 392, 531, 479, 521

[56] References Cited

U.S. PATENT DOCUMENTS

| | | | |
|---|---|---|---|
| 3,686,419 | 8/1972 | Duyfjes et al. | 514/764 |
| 3,979,324 | 9/1976 | Herber | 252/364 |
| 4,176,189 | 11/1979 | Itaya et al. | 514/389 |
| 4,215,009 | 7/1980 | Spaziante | 252/364 |
| 4,699,813 | 10/1987 | Cavezzan | 428/447 |
| 4,741,966 | 5/1988 | Cavezzan | 525/478 |
| 4,826,674 | 5/1989 | Albanese | 424/45 |
| 4,839,166 | 6/1989 | Grollier | 424/70 |
| 4,871,766 | 10/1989 | Tsuda et al. | 514/521 |
| 4,904,464 | 2/1990 | Albanese | 514/75 |

OTHER PUBLICATIONS

Aqueous pour-on formulation UK Patent App. #GB 2109236A.
Chemical Abstracts, vol. 95, No. 13, Sep. 28, 1981, p. 220, Resume No. 110186J.
Chemical Abstracts, vol. 94, No. 25, Jun. 22, 1981, p. 164, Resume No. 203850R.
Chemical Abstracts, vol. 90, No. 3, Jan. 15, 1979, p. 187, Resume No. 17690F.

*Primary Examiner*—Thurman K. Page
*Assistant Examiner*—Wm. Benston
*Attorney, Agent, or Firm*—Stevens, Davis, Miller & Mosher

[57] ABSTRACT

An insecticidal composition for aerosols comprises 2,4-dioxo-1-(2-propynyl)imidazolidin-3-ylmethyl chrysanthemate as an active ingredient and an organic solvent containing at least one aromatic hydrocarbon having 12 to 20 carbon atoms and kerosene in a weight ratio of said aromatic hydrocarbon to kerosene of 1:20 to 4:1. The aerosol according to the present invention has an excellent insecticidal activity.

11 Claims, No Drawings

INSECTICIDAL AEROSOL

The present invention relates to an insecticidal composition for aerosols. 2,4-Dioxo-1-(2-propynyl-)imidazolidin-3-ylmethyl chrysanthemate having the following formula (hereinafter referred to as Compound A),

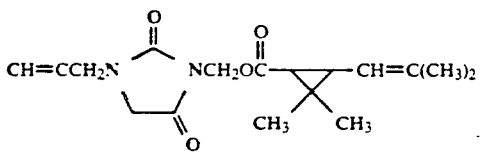

is a compound disclosed in U.S. Pat. No. 4,176,189. This compound is known to be usable as an active ingredient for insecticidal aerosols. Since, however, the aerosols containing the same are not always satisfactory in the insecticidal activity, they are not yet put to practical use.

According to the present invention, there are provided an insecticidal composition which comprises (A) 2,4-dioxo-1-(2-propynyl)imidazolidin-3-ylmethyl chrysanthemate as an insecticidally active ingredient and (B) an organic solvent containing at least one aromatic hydrocarbon having 12 to 20 carbon atoms and kerosene, the weight ratio of said aromatic hydrocarbon to said kerosene being 1:20 to 4:1, and an insecticidal aerosol containing said composition.

Compound A used in the present invention has various optical isomers and geometrical isomers. Therefore, any one of the isomers which have an insecticidal activity and the mixtures containing thereof can be used for the present invention. The content of Compound A in the insecticidal composition of the present invention is not critical, but it is preferably 0.0001 to 2.0% by weight, more preferably 0.01 to 1.0% by weight based on the total weight of the insecticidal composition.

The aromatic hydrocarbon used as a solvent is the aromatic hydrocarbon having 12 to 20 carbon atoms. Specific examples thereof are octylbenzene, dodecylbenzene, phenylxylylethane, etc.

The term "kerosene" refers to a mixture of hydrocarbons having a boiling point of 100° to 350° C., which mixture is a fraction between gasoline and the fuel oil obtained by the distillation of petroleum.

Usually the boiling point of kerosene used as a solvent of aerosols is 180° C. to 280° C.

In the insecticidal composition of the present invention, the weight ratio of aromatic hydrocarbon to kerosene is 1:20 to 4:1, preferably 1:12 to 4:1.

The insecticidal composition of the present invention may further be blended with insecticides other than Compound A, synergists, perfumes, fungicides, etc. Specific examples of the insecticides are 3-allyl-2-methyl-4-oxocyclopent-2-enyl chrysanthemate (allethrin), 3,4,5,6-tetrahydrophthalimidemethyl chrysanthemate (tetramethrin), 2-methyl-4-oxo-3-(2-propynyl)cyclopent 2-enyl chrysanthemate (prallethrin), 3-phenoxybenzyl chrysanthemate (phenothrin), 5-benzyl-3-furylmethyl chrysanthemate (resmethrin), α-cyano-3-phenoxybenzyl chrysanthemate (cyphenothrin), 3-phenoxybenzyl 3-(2,2-dichlorovinyl)-2,2-dimethylcyclopropanecarboxylate (permethrin), α-cyano-3-phenoxybenzyl 3-(2,2-dichlorovinyl)2,2-dimethylcyclopropanecarboxylate (cypermethrin), α-cyano-4-fluoro-3-phenoxybenzyl 3-(2,2-dichlorovinyl)-2,2dimethylcyclopropanecarboxylate (cyfluthrin), propoxur, dichlorvos, fenitrothion and the like.

The insecticidal composition of the present invention is prepared by mixing Compound A, at least one aromatic hydrocarbon having 12 to 20 carbon atoms, kerosene and optionally insecticides other than Compound A, synergists, perfumes, fungicides, etc. at room temperature or under heating.

The insecticidal composition of the present invention is suitably used as an insecticidal composition for aerosols by putting it in an aerosol can, mounting a valve portion on the can and charging a propellant under pressure into the can through the valve portion.

Specific examples of the propellant are liquefied petroleum gas (LPG), dimethyl ether (DME), carbon dioxide gas, nitrogen gas, etc. Of these, liquefied petroleum gas (LPG) and dimethyl ether (DME) are preferred.

The content of the propellant in the insecticidal composition of the present invention is not critical, but it is preferably 20 to 60% by weight based on the total weight of the composition.

The insecticidal composition of the present invention can be used not only in trigger sprayers, but also in novel spray systems such as EXXEL ®, a system comprising forcing out an insecticidal solution by the elastic power of rubbers developed by Container Industries in USA, and PROZON ®, a system comprising spraying an insecticidal solution by air fed by an electric pump developed by Oeco-tech in West Germany.

The present invention will be illustrated in more detail with reference to the following examples and comparative examples, but it is not limited to these examples only.

In the following examples, parts are by weight.

EXAMPLE 1

0.3 Part of Compound A containing a d-trans acid moiety, 5.0 parts of dodecylbenzene and 54.7 parts of kerosene were mixed with heating to prepare an insecticidal composition. The composition thus obtained was put in an aerosol can, a valve portion was mounted on the can and 40.0 parts of LPG was charged into the can under pressure through the valve portion to obtain an aerosol.

Table 1 shows the contents of the insecticidal compositions for aerosols obtained in the same manner as above.

TABLE 1

| | Content (part by weight) | | | |
|---|---|---|---|---|
| | Active ingredient Compound A (containing a d-trans acid moiety) | Solvent | | Propellant LPG |
| | | Dodecylbenzene | Phenylxylylethane | Kerosene | |
| Example | | | | | |
| 1 | 0.3 | 5.0 | — | 54.7 | 40.0 |
| 2 | 0.3 | 20.0 | — | 39.7 | 40.0 |
| 3 | 0.3 | 30.0 | — | 29.7 | 40.0 |
| 4 | 0.3 | 45.0 | — | 14.7 | 40.0 |
| 5 | 0.3 | — | 5.0 | 54.7 | 40.0 |
| 6 | 0.3 | — | 20.0 | 39.7 | 40.0 |
| 7 | 0.3 | — | 30.0 | 29.7 | 40.0 |
| 8 | 0.3 | — | 45.0 | 14.7 | 40.0 |

TABLE 1-continued

| | Content (part by weight) | | | | |
|---|---|---|---|---|---|
| | Active ingredient Compound A (containing a d-trans acid moiety) | Solvent | | | Propellant LPG |
| | | Dodecyl-benzene | Phenyl-xylyl-ethane | Kero-sene | |
| Comparative Example | | | | | |
| 1 | 0.3 | 1.0 | — | 58.7 | 40.0 |
| 2 | 0.3 | 59.7 | — | — | 40.0 |
| 3 | 0.3 | — | 1.0 | 58.7 | 40.0 |
| 4 | 0.3 | — | 59.7 | — | 40.0 |
| 5 | 0.3 | — | — | 59.7 | 40.0 |

With the aerosols obtained in Examples 1 to 8 and Comparative Examples 1 to 5, the knock-down efficacy (50% knock-down time) on flies and mosquitoes was examined by the CSMA aerosol test method (Peet Grady's chamber method). The results are shown in Table 2.

TABLE 2

| | $KT_{50}$ on fly (min) | $KT_{50}$ on mosquito (min) |
|---|---|---|
| Example | | |
| 1 | 2.3 | 3.5 |
| 2 | 1.8 | 2.7 |
| 3 | 2.0 | 2.2 |
| 4 | 1.8 | 3.6 |
| 5 | 2.1 | 4.4 |
| 6 | 1.8 | 3.3 |
| 7 | 1.9 | 3.0 |
| 8 | 2.0 | 3.5 |
| Comparative Example | | |
| 1 | 9.0 | 27.3 |
| 2 | 4.6 | 6.2 |
| 3 | 9.5 | 68.3 |
| 4 | 4.0 | 10.3 |
| 5 | 13.4 | 58.1 |

EXAMPLE 9

0.3 Part of Compound A containing a d-trans acid moiety, 0.1 part of phenothrin, 20.0 parts of dodecyl-benzene and 39.6 parts of kerosene were mixed with heating to prepare an insecticidal composition. The composition thus obtained was put in an aerosol can, a valve portion was mounted on the can and 40.0 parts of LPG and charged into the can under pressure through the valve portion to obtain an aerosol.

Table 3 shows the contents of the insecticidal compositions for aerosols obtained in the same manner as above.

TABLE 3

| | Content (part by weight) | | | | | | | | | |
|---|---|---|---|---|---|---|---|---|---|---|
| | Active ingredient | | | | Solvent | | | | Propellant | |
| | Compound A (containing a d-trans acid moiety) | Alle-thrin | Pheno-thrin | Feni-tro-thion | Dode-cyl-ben-zene | Octyl-ben-zene | Phenyl-xylyl-ethane | Kero-sene | LPG | DME |
| Example | | | | | | | | | | |
| 9 | 0.3 | — | 0.1 | — | 20.0 | — | — | 39.6 | 40.0 | — |
| 10 | 0.3 | 0.1 | — | — | 20.0 | — | — | 39.6 | 40.0 | — |
| 11 | 0.3 | — | — | 0.3 | 30.0 | — | — | 19.4 | 50.0 | — |
| 12 | 0.3 | — | 0.1 | — | — | 20.0 | — | 39.6 | 40.0 | — |
| 13 | 0.3 | 0.1 | 0.1 | — | 20.0 | — | — | 29.5 | 25.0 | 25.0 |
| 14 | 0.3 | — | 0.1 | — | 10.0 | — | 10.0 | 29.6 | 25.0 | 25.0 |

Aerosols obtained in Examples 9 to 14 were examined for the knock-down efficacy on flies and mosquitoes by the CSMA aerosol test method. The results are shown in Table 4.

TABLE 4

| | $KT_{50}$ on fly (min) | $KT_{50}$ on mosquito (min) |
|---|---|---|
| Example | | |
| 9 | 1.7 | 2.3 |
| 10 | 1.3 | 1.2 |
| 11 | 1.6 | 1.9 |
| 12 | 1.5 | 2.6 |
| 13 | 1.3 | 1.1 |
| 14 | 1.5 | 2.1 |

Table 5 shows the contents of the insecticidal compositions for aerosols obtained in the same manner as in Example 1.

TABLE 5

| | Content (part by weight) | | | | | | | |
|---|---|---|---|---|---|---|---|---|
| | Active ingredient Compound A (containing a d-trans acid moiety) | Solvent | | | | | | Propellant LPG |
| | | Xylene | Toluene | Tri-methyl-benzene | Butyl-ben-zene | Octyl-benzene | Kero-sene | |
| Example | | | | | | | | |
| 15 | 0.3 | — | — | — | — | 20.0 | 39.7 | 40.0 |
| Comparative Example | | | | | | | | |
| 6 | 0.3 | 20.0 | — | — | — | — | 39.7 | 40.0 |
| 7 | 0.3 | — | 20.0 | — | — | — | 39.7 | 40.0 |

TABLE 5-continued

| | Content (part by weight) | | | | | | | |
|---|---|---|---|---|---|---|---|---|
| | Active ingredient Compound A (containing a d-trans acid moiety) | Solvent | | | | | | Propellant LPG |
| | | Xylene | Toluene | Trimethylbenzene | Butylbenzene | Octylbenzene | Kerosene | |
| 8 | 0.3 | — | — | 20.0 | — | — | 39.7 | 40.0 |
| 9 | 0.3 | — | — | — | 20.0 | — | 39.7 | 40.0 |

Aerosols obtained in Example 15 and Comparative Examples 6 to 9 were examined for the knock-down efficacy on flies and mosquitoes by the CSMA aerosol test method. The results are shown in Table 6.

TABLE 6

| | $KT_{50}$ on fly (min) | $KT_{50}$ on mosquito (min) |
|---|---|---|
| Example | | |
| 15 | 1.7 | 2.6 |
| Comparative Example | | |
| 6 | 7.2 | 9.7 |
| 7 | 6.5 | 8.3 |
| 8 | 8.0 | 10.3 |
| 9 | 6.0 | 8.2 |

What is claimed is:

1. An insecticidal composition which comprises
(A) an insecticidally effective amount of 2,4-dioxo-1-(2-propynyl)imidazolidin-3-ylmethyl chrysanthemate as an insecticidally active ingredient and
(B) an organic solvent containing at least one aromatic hydrocarbon having 12 to 20 carbon atoms and kerosene, the weight ratio of said aromatic hydrocarbon to said kerosene being 1:20 to 4:1.

2. A composition according to claim 1, wherein the composition further contains an insecticidally effective amount of at least one additional insecticide selected from the group consisting of 3-allyl-2-methyl-4-oxocyclopent-2-enyl chrysanthemate (allethrin), 3,4,5,6-tetrahydrophthalimidemethyl chrysanthemate (tetramethrin), 2-methyl-4-oxo-3-(2-propynyl)cyclopent-2-enyl chrysanthemate (prallethrin), 3-phenoxybenzyl chrysanthemate (phenothrin), 5-benzyl-3-furylmethyl chrysanthemate, (resmethrin) α-cyano-3-phenoxybenzyl chrysanthemate(cyphenothrin), 3-phenoxybenzyl 3-(2,2-dichlorovinyl)-2,2-dimethylcyclopropanecarboxylate (permethrin), α-cyano-3-phenoxybenzyl 3-(2,2-dichlorovinly)-2,2-dimethylcyclopropanecarboxylate (cypermethrin), α-cyano-4-fluoro3-phenoxybenzyl 3-(2,2-dichlorovinyl)-2,2-dimethylcyclopropanecarboxylate(cyfluthrin), propoxur, dichlorvos and fenitrothion.

3. An insecticidal aerosol consisting essentially of an insecticidal composition according to claim 1 and a propellant.

4. An insecticidal aerosol consisting essentially of an insecticidal composition according to claim 2 and a propellant.

5. An aerosol according to claim 3, wherein the content of the insecticidally active ingredient is 0.0001 to 2.0% by weight based on the total weight of the composition.

6. An aerosol according to claim 4, wherein the content of the 2,4-dioxo-1-(2-propynyl)imidazolidin-3-ylmethyl chrysanthemate is 0.0001 to 2.0% by weight based on the total weight of the composition.

7. A composition according to claim 1, wherein said aromatic hydrocarbon is selected from the group consisting of octylbenzene, dodecylbenzene and phenylxylylethane.

8. A composition according to claim 2, wherein said aromatic hydrocarbon is selected from the group consisting of octylbenzene, dodecylbenzene and phenylxylylethane.

9. An aerosol according to claim 3, wherein said aromatic hydrocarbon is selected from the group consisting of octylbenzene, dodecylbenzene and phenylxylylethane.

10. An aerosol according to claim 4, wherein said aromatic hydrocarbon is selected from the group consisting of octylbenzene, dodecylbenzene and phenylxylylethane.

11. A composition according to claim 1, wherein the ratio of (A) to (B) is 3:1 to 1:1.

* * * * *